US006737371B1

(12) United States Patent
Planck et al.

(10) Patent No.: US 6,737,371 B1
(45) Date of Patent: May 18, 2004

(54) HERNIA IMPLANT, METHOD FOR ITS MANUFACTURE AND USE IN SURGERY

(75) Inventors: Heinrich Planck, Nuertingen (DE); Erhard Mueller, Stuttgart (DE); Anette Arnold, Esslingen (DE); Hans-Gerd Schmees, Wannweil (DE); Bernhard Leibl, Ostfildern (DE)

(73) Assignee: Deutsche Institute fur Textil-und Faserforschung Stuttgart Stiftung des offentlichen Rechts, Denkendorf (DE)

( * ) Notice: Subject to any disclaimer, the term of this patent is extended or adjusted under 35 U.S.C. 154(b) by 117 days.

(21) Appl. No.: 09/705,925

(22) Filed: Nov. 6, 2000

(30) Foreign Application Priority Data

Nov. 10, 1999 (DE) .......................... 199 54 166

(51) Int. Cl.[7] .................... D04G 1/00; B32B 5/26; B32B 5/02; B32B 3/00; D02G 3/00; A61F 2/02
(52) U.S. Cl. .................. 442/304; 428/373; 428/71; 428/374; 428/375; 428/376; 428/378; 442/1; 442/318; 442/319; 442/304; 442/66; 623/1; 623/11; 623/11.11; 623/66; 623/13; 623/14
(58) Field of Search ................ 623/1, 11, 66, 623/13, 14; 428/373, 11, 374, 375, 376, 378; 442/1, 318, 319, 304, 66

(56) References Cited

U.S. PATENT DOCUMENTS 5,326,355 A * 7/1994 Landi .......................... 623/66
5,383,925 A * 1/1995 Schmitt ........................ 623/1
5,569,273 A   10/1996 Titone et al.
5,593,441 A   1/1997 Lichtenstein et al.
5,616,391 A * 4/1997 Amesz et al. ................. 428/71
5,686,090 A   11/1997 Schilder et al.
6,162,537 A * 12/2000 Martin et al. ................ 428/373
6,162,962 A   12/2000 Hinsch et al.

FOREIGN PATENT DOCUMENTS

| DE | 198 32 643 | 10/1997 |
| DE | 196 13 730 | 1/2000 |
| GB | 2 222 954 | 3/1990 |
| WO | WO 99/51163 | 10/1999 |

OTHER PUBLICATIONS

Barie, P. S., Thompson, W. A., and Mack, C. A., *Planned laparoscopic repair of a spigellian hernia using a composite prosthesis*. Journal of Laparoendoscopic Surgery, (Oct. 1994) 4 (5) 359–63. (Information taken from MEDLINE Abstract).

* cited by examiner

Primary Examiner—Cheryl A. Juska
Assistant Examiner—Lynda Salvatore
(74) Attorney, Agent, or Firm—Nath & Associates PLLC; Gary M. Nath; Jerald L. Meyer (57) ABSTRACT

A flat hernia implant with a flexible fabric formed from at least two textile fabric structures constructed substantially independently of one another and firmly interconnected over the entire surface area of the hernia implant so as to form a composite structure, is made available for use in surgery.

30 Claims, 8 Drawing Sheets

HERNIA IMPLANT, METHOD FOR ITS MANUFACTURE AND USE IN SURGERY

The present invention relates to a hernia implant, a method for its manufacture and its use in surgery.

Hernia is a frequently encountered illness. It generally involves a passage of organs or organ parts out of the natural body cavity through a preformed or acquired gap. Inguinal, umbilical and cicatricial hernias are the most frequently encountered external hernias, in which the hernial sac is always surrounded by peritoneum. The reasons for hernias occurring are in particular muscular or connective tissue weaknesses in conjunction with strains, slackening caused by age, congenital weakening of the abdominal wall or inadequate cicatrization following an abdominal incision (cicatricial hernia).

An effective treatment is possible in most cases by a surgical operation, where the content of the hernia is passed back from the hernial sac into the abdomen and the hernial orifice is sealed. The sealing of the hernial orifice generally takes place by means of a suture.

However, this surgical procedure suffers from the disadvantage that in up to 20% of cases a further hernia can occur, which is known as the hernial recidivation or recurrence.

Due to this unsatisfactory recurrence rate following conventional hernia operations, in modern hernia surgery use is being increasingly made of synthetic reinforcing materials for reconstructing the abdominal wall. An important part is played by nets of polyester, polypropylene and polytetrafluoroethylene.

Although the use of such nets has clearly led to a marked reduction in the recurrence rate, these implants give rise to problems as a result of possible infections, the formation of hard scar scales, displacements or fistula formations. Particularly in the hypogastric region, due to leg mobility, a supply with a very elastic implant and elastic scar formation is necessary for rapid healing and freedom from complaints on the part of the patient.

The problem of the invention is to make available a hernia implant for use during surgical operations, which overcomes the difficulties encountered with the prior art implants, which is easy and inexpensive to manufacture and which is easy to handle in standard surgical procedures.

This problem is solved by a hernia implant for use in surgery having a flexible fabric, which is formed from at least two substantially independently constructed textile fabric structures, which are firmly interconnected over the entire surface of the implant so as to form a composite structure. Such a composite structure offers a high initial implant strength.

Preferably, in the hernia implant according to the invention, substantially all the composite components are formed from monofilaments and preferably exclusively from monofilaments. The use of monofilaments in implant structures compared with multifilament yarns is characterized by a reduced infection susceptibility, because germs find no colonization spaces such as are encountered between single fibres.

Advantageously a monofilament can have a thickness of 10 to 500 $\mu$m, particularly 100 to 150 $\mu$m. According to an embodiment of the invention the monofilaments of the independent textile fabric structures essentially have the same thicknesses. According to another embodiment of the invention the monofilaments of the independent textile fabric structures can have different thicknesses.

According to the invention the fabric can be produced by a textile method, particularly knitting, weaving or braiding. Such procedures are known to the expert, so that a detailed description is not provided here. The invention gives preference to knitted fabrics.

Thus, in a preferred embodiment the hernia implant is formed from knitwear, particularly knit goods. This permits a simple, inexpensive manufacture according to known, proven procedures using conventional machines and tools.

Advantageously the individual textile fabric structures can be constructed in the form of net structures, particularly knitted net structures. Knitwear is characterized compared with other textile structures by a higher flexibility of the fabric, which is desirable for uses in medicine. In an embodiment the at least two nets can have substantially the same structure. In another preferred embodiment the at least two nets can have different structures. Differences in the structure can in particular be formed by different binding of the filamentary material in the textile fabric.

The openings or pores of the nets can have random polygonal or oval shapes. For example the net structure can be rhombic, latticed, honeycombed, circular or slot-shaped. Advantageously openings of at least one fabric structure preferably have a substantially hexagonal shape. A knitted net can e.g. have a honeycombed structure and hexagonal pores are surrounded by bridges formed from knitted monofilaments.

According to the invention the individual textile fabric structures can have a pore structure with pore sizes or opening sizes of 0.1 to 10 mm, particularly 0.5 to 5 mm. In an embodiment of the invention the pore sizes of the individual textile fabric structures can be substantially identical. In another preferred embodiment of the invention the pore sizes of the individual textile fabric structures can differ.

According to an embodiment of the invention the individual textile fabric structures can be produced according to the same procedure. According to a further embodiment of the invention the individual textile fabric structures can be produced according to different binding procedures. For example, in a preferred embodiment, one textile fabric is formed by knitting in accordance with the satin or atlas 2-row binding method. In another preferred embodiment one textile fabric can be formed by knitting according to the tulle fillet binding method. The production of the individual fabric structures with different binding methods permits in simple manner the formation of different pore shapes and sizes.

Advantageously the textile fabric structures can be interconnected by textile methods. Particular preference is given according to the invention to the textile fabric structures being interconnected by knitting. In this way fabric structures produced by knitting can be combined to form a composite in simple manner using the same machines and procedures.

According to the invention the textile fabric structures, particularly net structures, can be so mutually arranged that their structure pores, particularly openings do not align and in particular roughly overlap by half. The hernia implant according to the invention can be characterized in that the textile fabric structures, particularly net structures, overlap in both dimensions of the net planes. In this way, for the same weight per unit area, a fabric which is tighter with respect to the passage of substances such as body fluids, cells or microorganisms is obtained than when the net pores are oriented in aligned manner. In addition, a close-mesh textile structure facilitates the growing of the hernia implant into the body and consequently aids rapid healing.

In the case of knitting, such net structures can be produced in that two independent fabrics are constructed on mutually laterally displaced needles. In an embodiment fabrics can be produced with different mesh sizes. In this way e.g. in the internal pore size of a coarser meshed net can be located several meshes of a finer meshed net. With particular advantage such overlapping structures can be produced by the simultaneous knitting with different knitting constructions or bonds.

The hernia implant according to the invention can advantageously be characterized in that it is at least partly absorbable in vivo. The decomposition or degradation of a bioabsorbable polymer takes place by metabolic processes in the body of an animal or human. Body and tissue fluids participate in the reaction. As a result of hydrolysis the polymer chain is split into smaller and more easily soluble fragments. The fragments are further degraded, optionally accompanied by the participation of enzymatic processes. The degradation products are transported away by the metabolic system and are eliminated from the organism in the same way as other metabolic waste products. It is important for a good compatibility of the absorbable implant material by the patient, that during the degradation process no harmful metabolites are formed or concentrated.

In the case of the hernia implant according to the invention at least one of the textile fabric structures, particularly one having hexagonal openings, can be substantially formed from non-absorbable material and at least one further textile fabric structure can be substantially formed from absorbable material. The invention gives preference to an embodiment in which two independently formed fabric structures are provided, whereof one is formed from non-absorbable material and the other from absorbable material. It is also preferable according to the invention for the fabric structure of non-absorbable material to have hexagonal openings.

Advantageously absorbable filamentary material is used for joining the textile fabric structures. According to the invention the hernia implant can contain absorbable and non-absorbable material in a ratio of 90:10 to 10:90, particularly 30:70 to 70:30 and preferably 50:50.

Within 8 to 12 weeks following the introduction of the implant according to the invention, as a result of the degradation reactions on the absorbable material in the body of the patient there is a hernia implant strength loss. Due to biochemical degradation, there is chain splitting and weight loss with respect to resorbable components in the polymer filamentary material. This leads to a progressive deterioration of mechanical characteristics such as e.g. the strength and flexural rigidity. The implanted fabric becomes increasingly elastic, can better adapt to local circumstances in the abdomen and can perform movements made by the patient.

Advantageously in the hernia implant according to the invention the absorbable component is completely degraded in vivo after 6 to 50 weeks, particularly 8 to 12 weeks.

Advantageously as a result of the degradation of the absorbable material in vivo, it is possible to increase the pore size of the hernia implant. In this way it is possible to at least compensate a stiffening by the growing in of body cells by a partial degradation of the composite structure. Over a period of time there can be a cicatrization of the hernia implant with the abdominal wall. The resulting union of abdominal wall and implant contributes to the stabilization of the said wall and consequently ensures the success of the treatment.

With advancing absorbable material degradation an implant weight loss occurs, which is revealed in an increasingly open-cell nature of the structure. Following complete degradation of the absorbable component a fabric structure of non-absorbable material is left behind. Preferably the fabric structure of non-absorbable material is formed with a hexagonal pore structure. A hexagonal structure is particularly advantageous for a hernia implant remaining in vivo. In this way through the choice of the textile construction of the individual fabric structures of the hernia implant union of non-absorbable and absorbable material, it is possible to obtain an optimum structure for growing in and adaptation to physiological circumstances of the implant part remaining permanently in the patient's body. Preferably the components of the implant composite structure are chosen in such a way that following resorption of the biodegradable material a hernia implant remains in the body, whose mechanical characteristics are adapted to the natural characteristics of the abdominal wall.

In the present invention an embodiment is particularly advantageous where a fabric structure of non-absorbable material and at least one further fabric structure of absorbable material are formed into a hernia implant composite structure. A further advantage of the invention is the use of monofilaments for forming the textile fabric structures. Compared with the individual filaments in a multifilament, such as are known from the prior art, a monofilament has a greater thickness. Thicker monofilaments have a higher flexural rigidity, which has an effect on the handling properties of a resulting textile fabric. For a large-area, creaseless and stress-free insertion of flat hernia implants in the abdomen of a patient, reliable handling, i.e. a certain rigidity and strength of the implant, in addition to flexibility is desired. By the use of absorbable monofilaments in an implant composite structure according to the invention such a desired stability is achieved.

During the biochemical resorption of the degradable components the mechanical strength and rigidity of the hernia implant continuously decrease, i.e. the implant becomes more flexible, so that the patient is less stressed by the implant. Following the degradation of the absorbable material fraction, a flexible net with only a small amount of foreign material remains in the patient's body.

In a special embodiment the monofilament of absorbable material can be thicker than the monofilament of non-absorbable materials. According to the invention preference is given to an absorbable monofilament with a thickness of 100 to 250 $\mu$m. According to the invention, preference is given to a non-absorbable monofilament with a thickness of 100 to 250 $\mu$m. This makes it possible to minimize the foreign material quantity left behind following absorption of the biodegradable material. The absorbable and non-absorbable monofilaments can have the same or different thicknesses.

According to the invention the non-absorbable material can have a weight per unit area of up to 50 g/m, particularly up to 40 g/m. The non-absorbable material can have a strength of 16 to 50 N/cm. The hernia implant according to the invention can have a bursting pressure of 100 to 300 kPa. The hernia implant according to the invention can have a bursting elongation or extension of 20 to 50 mm.

Advantageously the hernia implant according to the invention is characterized in that its extensibility, measured in the longitudinal, transverse and diagonal directions, differs by no more than 50% in each case and in particular have substantially identical values. The hernia implant according to the invention can also be characterized in that its tearing or tensile strength, measured in the longitudinal, transverse and diagonal directions, in each case differ by no more than 50% and in particular have substantially identical values.

In the case of the hernia implant according to the invention the non-absorbable material can be selected from the group comprising polypropylene, polytetrafluoroethylene, polytetrafluoroethylene-hexafluoropropylene copolymer, polyethylene terephthalate, polybutylene terephthalate, as well as their mixtures, copolymers and terpolymers. In a preferred embodiment of the invention the absorbable material is formed from monofilament polylactide fibres. In another preferred embodiment of the invention the absorbable material can be formed from monofilament fibres of polylactide-glycolide copolymer.

In the case of the implant according to the invention the absorbable material can be selected from the group comprising polyglycolide, polylactide, polydioxanone, polyhydroxybutyric acid, polycaprolactone, polytrimethylene carbonate, polytetramethylene carbonate, as well as their mixtures, copolymers and terpolymers. In a preferred embodiment of the invention the non-absorbable material is formed from monofilament polypropylene fibres.

According to a further development the hernia implant can contain an antimicrobiotic agent, such as e.g. an antibiotic. The administration of antibiotics more particularly serves to prevent infections. For prophylaxis and therapy with antibiotics use is made in the surgery field of e.g. cephalosporins such as cephazolin and cephamandol, netilmycin, penicillins such as oxacillin or mezlocillin, tetracycline, metronidazole or aminoglycosides such as gentamycin or neomycin, as well as e.g. rifampicin. In accordance with the given requirements, the experts can select one or more appropriate active agents. The hernia implant can also contain growth factors.

The present invention also relates to a method for the manufacture of a hernia implant for use in surgery comprising the formation of at least two independent textile fabric structures and the joining together of these textile fabric structures over their entire surface area in order to form a composite structure in the form of a flexible fabric. Preferably the textile fabric structures are in the form of knitwear and are particularly produced by knitting. The textile fabric structures can, according to the invention, be joined by textile procedures, particularly by knitting during their joint manufacture.

For use in surgery, the hernia implant modified according to the invention can be appropriately sterilized. An appropriate sterilization process can be constituted by conventional physical or chemical methods for inactivating microorganisms or a combination thereof. One possible sterilization process comprises treatment with ionizing radiation such as e.g. irradiation with gamma or beta rays in the range 0.1 to 10 mrad, particularly 0.8 to 2.5 mrad.

The invention also relates to the use of a hernia implant in surgery, particularly for the treatment of wall defects in body cavities, particularly abdominal wall defects.

To this end the hernia implant material modified according to the invention can be cut to a desired size and shape. Advantageously the surgical hernia implant according to the invention can be suitably packed cut to appropriate dimensions and ready for use. In practice, preferred dimensions of 15×30 cm or 30×30 cm are used.

For illustration purposes embodiments of the invention are shown in exemplified manner in the attached drawings.

Figure 1:
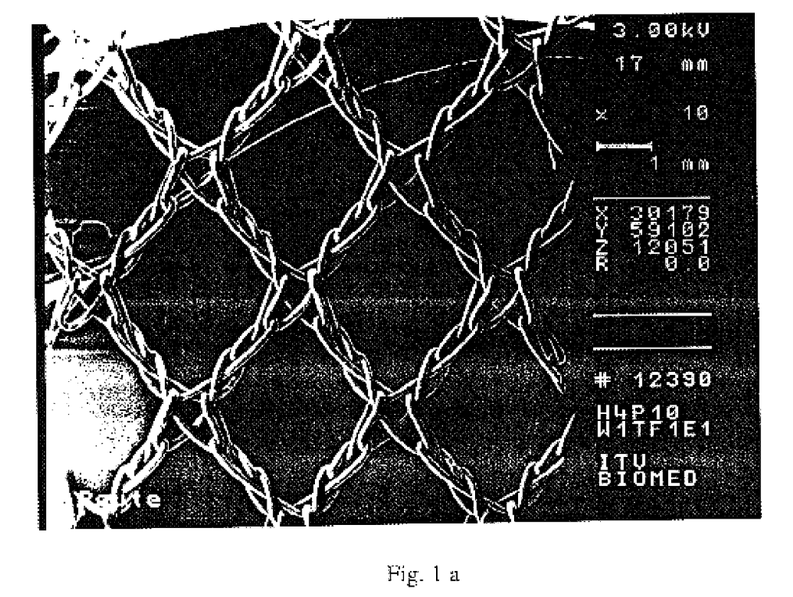
FIGS. 1a and 1b show the front/back of a knitted fabric structure of non-absorbable polypropylene in rhombic form.
Figure 2:
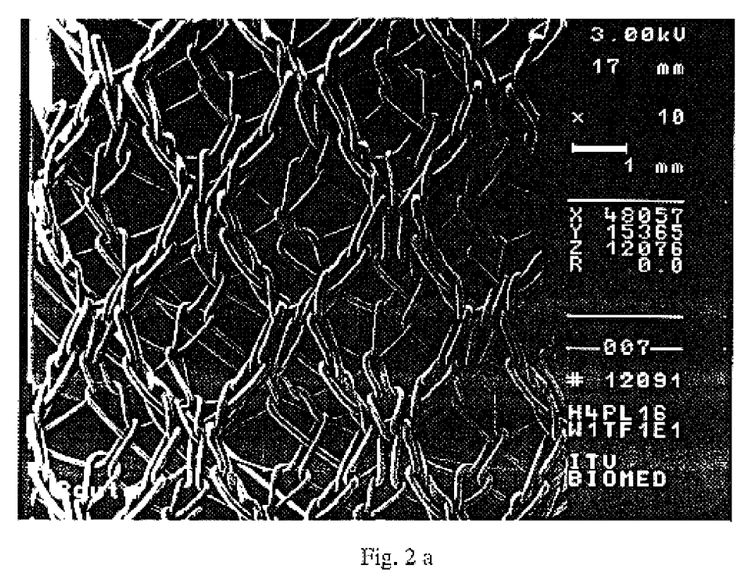
FIGS. 2a and 2b show the front/back of a partly absorbable hernia implant of non-absorbable polypropylene (PP), as shown in FIG. 1, and a fabric structure of absorbable polylactide (PLLA) in rhombic form knitted therewith. The PLLA knitted fabric overlaps the pore structure of the PP knitted fabric.
Figure 3:
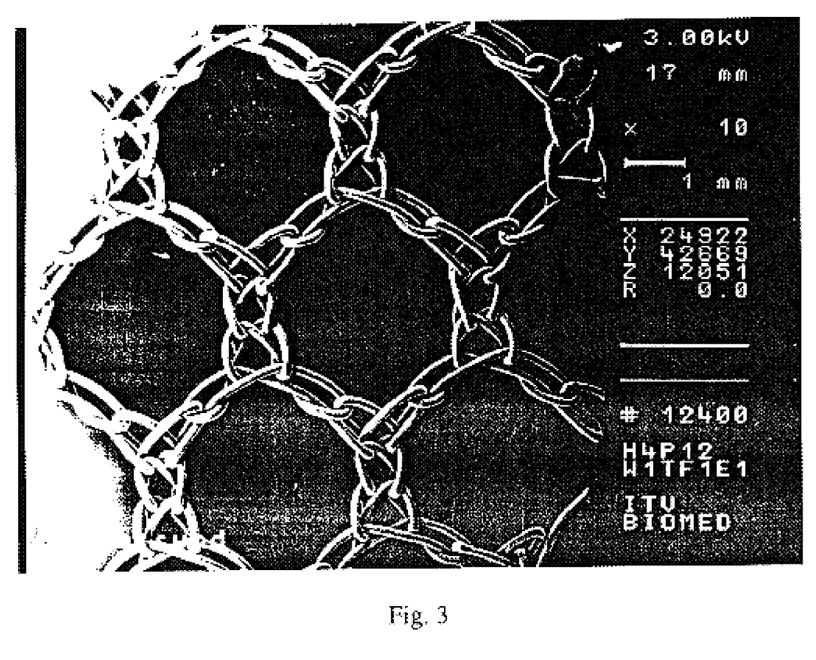
FIG. 3 shows a PP knitted fabric with a hexagonal structure.
Figure 4:
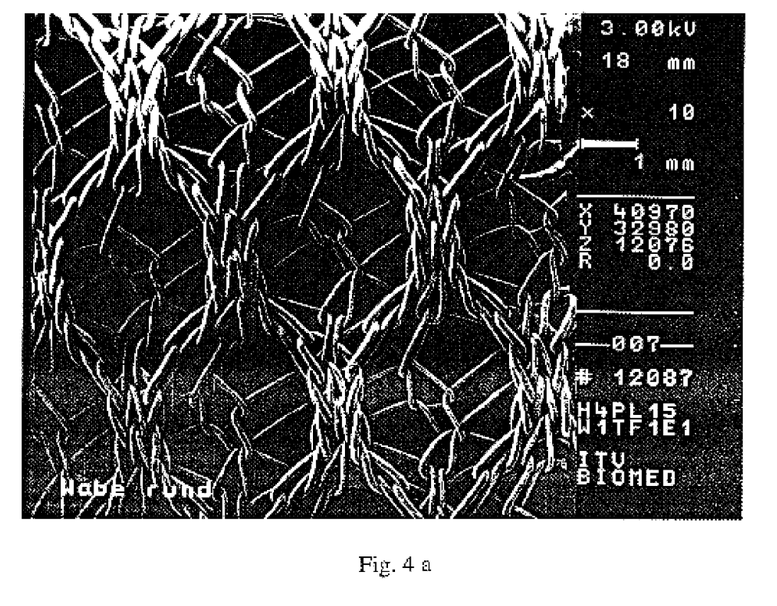
FIGS. 4a and 4b show the front/back of a partly absorbable hernia implant of non-absorbable PP, as shown in FIG. 3, and a honeycombed absorbable PLLA fabric structure knitted therewith.
Figure 5:
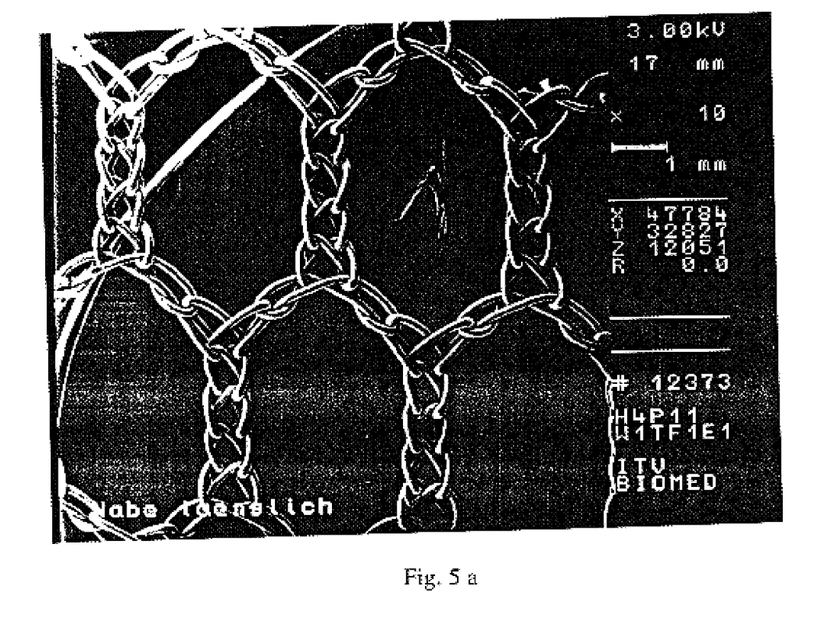
FIGS. 5a and 5b show the front/back of a knitted fabric structure of non-absorbable polypropylene with an elongated honeycombed structure.
Figure 6A:
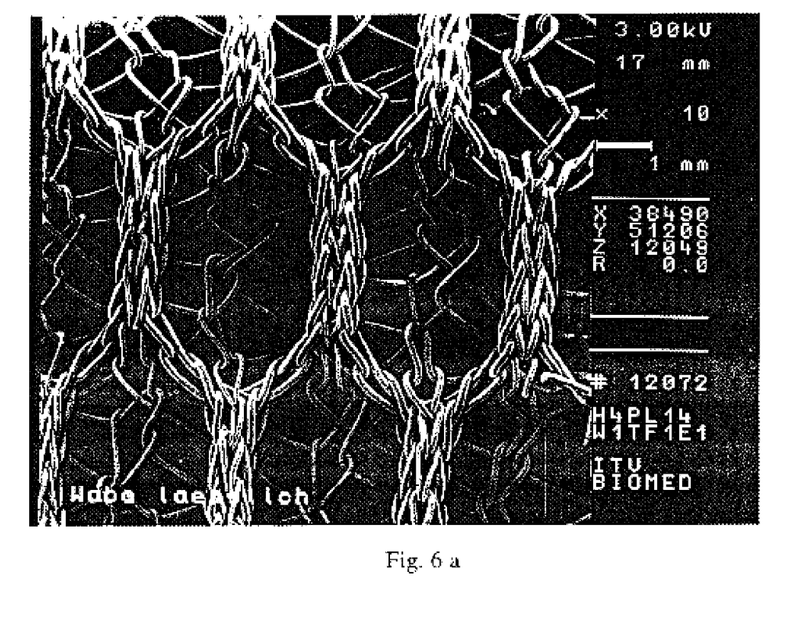
FIGS. 6a and 6b show the front/back of a partly absorbable hernia implant of non-absorbable PP, as shown in FIG. 5, and an absorbable PLLA fabric structure with an elongated honeycomb structure knitted therewith.
Figure 6B:
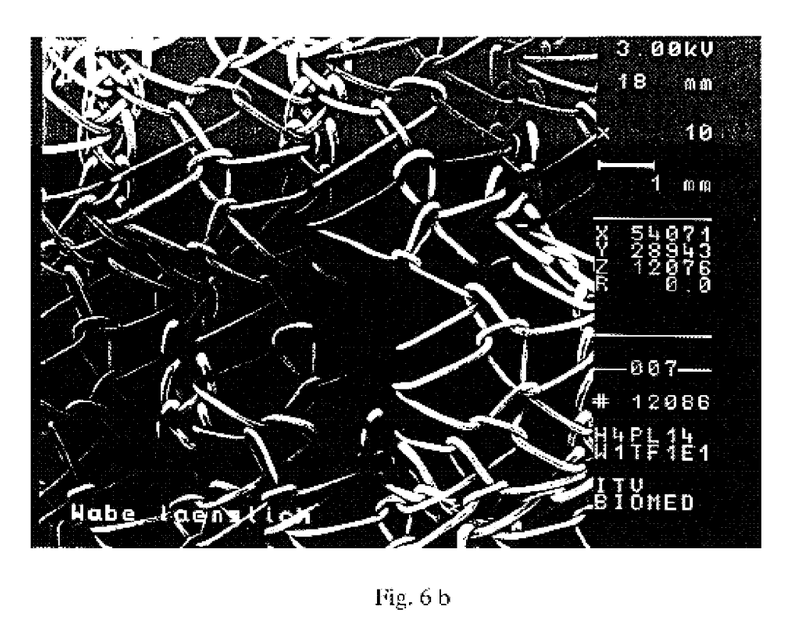
Figure 7:
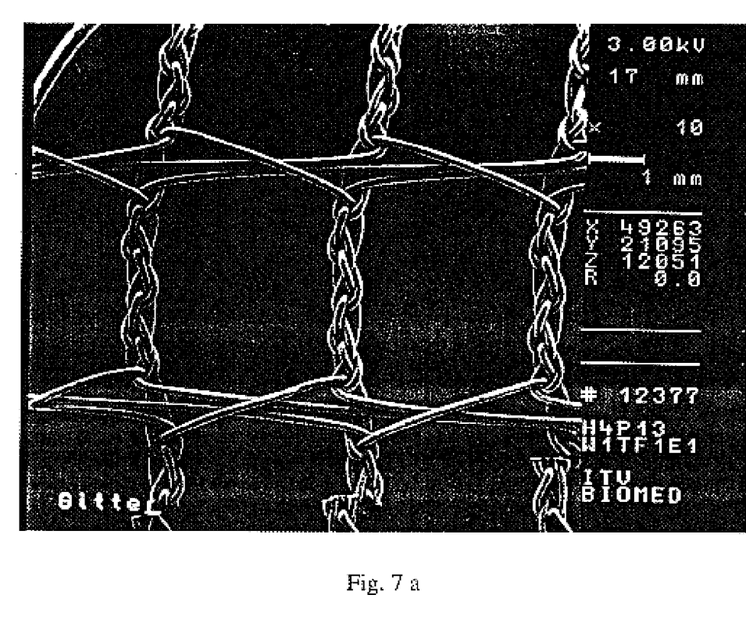
FIGS. 7a and 7b show the front/back of a knitted fabric structure of non-absorbable, latticed polypropylene. The longitudinally directed strands in the drawings are formed from knitted threads and the cross-connections in the lattice are formed from monofilaments.
Figure 8:
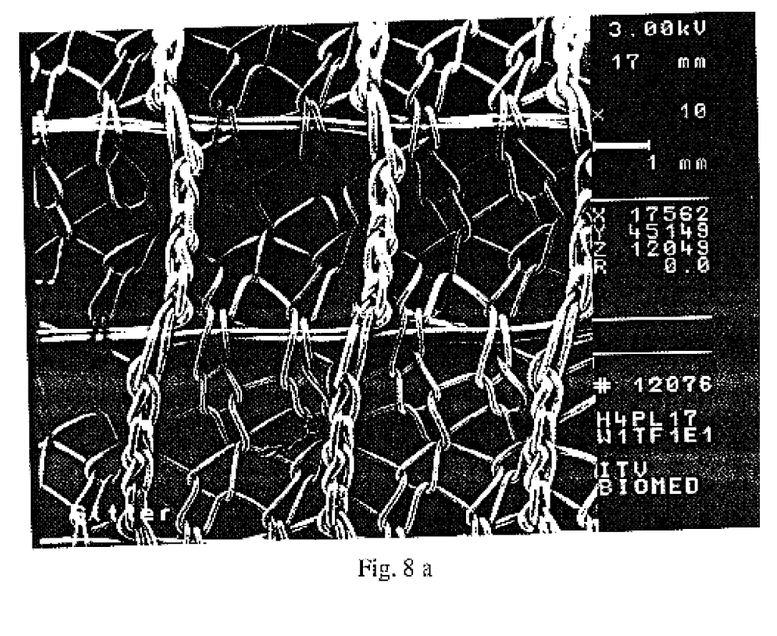
FIGS. 8a and 8b show the front/back of a partly absorbable hernia implant of non-absorbable PP, as shown in FIG. 7, and an absorbable PLLA fabric structure knitted thereto. An absorbable fine structure is superimposed on a bearing coarse structure.

Further features of the invention can be gathered from the following description of a preferred embodiment. The individual features of the invention claimed in the subclaims can in each case be implemented singly or in the form of subcombinations in an embodiment of the invention. The following example serves for illustration purposes and is not to be understood as a restriction. Modifications and changes apparent to the expert are possible without leaving the scope of the invention.

EXAMPLE

Monofilaments of polylactide (PLLA) and polypropylene (PP) are processed on a warp knitting machine for manufacturing a hernia composite net of absorbable and non-absorbable biocompatible polymer material. The satin or atlas 2-row method is used for the absorbable PLLA fabric, for which the warp arrangement is 2-0/4-6/8-10/6-4/2-0/4-6/8-10/6-4, so that this guide bar works on needles 2, 4, 6, 8, 10 etc. For the non-absorbable PP fabric working takes place according to the tulle fillet procedure, where the warp arrangement is one guide bar 2-0/4-6/2-0/4-6/8-10/6-4/8-10/6-4, and second guide bar 8-10/6-4/8-10/6-4/2-0/4-6/2-0/4-6, so that both guide bars work on needles 1, 3, 5, 7, 9 etc. The atlas 2-row and tulle fillet are not worked on the same needles, but are instead laterally displaced by one needle. Thus, the absorbable knitted fabric forms a mesh structure with smaller pore sizes compared with the mesh structure of the non-absorbable knitted fabric. Between each of the bridges of the honeycomb structure of non-absorbable material are in each case located several meshes of absorbable material. The two knitted fabrics are interconnected by underlaps. Underlapping in vivo permits a degradation of the absorbable knitted fabric without interacting with the non-absorbable knitted fabric.

What is claimed is:

1. Hernia implant for use in surgery comprising a flexible fabric formed from at least two substantially independently constructed textile fabric structures, which are firmly interconnected over the entire surface of the hernia implant to form a composite structure;

wherein the composite components are formed from monofilaments having a thickness of about 10 to about 500 µm;

said textile fabric structures are formed as net structures with at least two net structures having a substantially different structure from each other and at least one of said textile fabric structures having a pore; and said textile fabric structures are interconnected by knitting and are associated in a way that their structure pores are not aligned;

wherein said hernia implant is made of at least one material which is at least partly absorbable in vivo and where, by way of in vivo degradation of said absorbable material, pore sizes in said hernia implant increase; and wherein said hernia implant has a bursting pressure of 100 to 300 kPa.

2. Hernia implant according to claim 1, wherein the thickness is 100 to 150 µm.

3. Hernia implant according to claim 1, wherein the fabric structures are knitted net structures.

4. Hernia implant according to claim 1, wherein the nets are produced by different binding procedures.

5. Hernia implant according to claim 1, wherein the openings have a substantially hexagonal shape.

6. Hernia implant according to claim 1, wherein the individual textile fabric structures have a pore structure with pore sizes of 0.1 to 10 mm.

7. Hernia implant according to claim 6, wherein the pore sizes are 0.5 to 5 mm.

8. Hernia implant according to claim 1, wherein the individual textile fabric structure are produced by different binding procedures.

9. Hernia implant according to claim 1, wherein the structure pores are openings and overlap roughly by half.

10. Hernia implant according to claim 1, wherein at least one of the textile fabric structures is formed substantially from non-absorbably material and at least one other of the textile fabric structures is substantially formed from absorbable material.

11. Hernia implant according to claim 10, wherein a textile fabric structure having hexagonal openings is formed substantially from non-absorbable material.

12. Hernia implant according to claim 1, wherein absorbable and non-absorbable materials are present in a ratio of 90:10 to 10:90.

13. Hernia implant according to claim 12, wherein the materials are present in ratio of 30:70 to 70:30.

14. Hernia implant according to claim 12, wherein the materials are present in ratio of 50:50.

15. Hernia implant according to claim 1, wherein a filamentary material for joining the textile fabric structures is formed from absorbable material.

16. Hernia implant according to claim 1, wherein a non-absorbable material has a weight per unit area of up to 50 g/m².

17. Hernia implant according to claim 16, wherein the material weight per unit area is up to 40 g/m².

18. Hernia implant according to claim 1, wherein a non-absorbable material has a strength of 16 to 50 N/cm.

19. Hernia implant according to claim 1, wherein it has a bursting elongation of 20 to 50 mm.

20. Hernia implant according to claim 1, wherein its extensibility measures in longitudinal, transverse and diagonal directions in each case differs by no more than 50%.

21. Hernia implant according to claim 20, wherein the extensibility values are substantially identical values.

22. Hernia implant according to claim 1, wherein its tearing strength measured in longitudinal, transverse and diagonal directions in each case differs by no more than 50%.

23. Hernia implant according to claim 22 wherein the strength values are substantially identical.

24. Hernia implant according to claim 1, wherein a non-absorbable material is selected from the group comprising polypropylene, polytetrafluroethylene, polytetrafluoroethylene-hexafluoropropylene copolymer, polyethylene terephthalate, polybutylene terephthalate, as well as their mixtures, copolymers and terpolymers.

25. Hernia implant according to claim 1, wherein an absorbable material is selected from the group comprising polyglycolide, polylactide, polydioxanone, polyhydroxybutyric acid, polycaprolactone, polytrimethylene carbonate, polytetramethylene carbonate, as well as their mixtures, copolymers and terpolymers.

26. Method for the manufacture of a hernia implant by forming at least two independent textile fabric structures and joining said textile fabric structures over their surface area to form a composite structure in the form of a flexible fabric;

wherein the composite components are formed from monofilaments having a thickness of about 10 to about 500 microns; said textile fabric structures are formed as net structures with at least two net structures having a substantially different structure from each other and at least one of said textile fabric structures having an opening; and said textile fabric structures are interconnected by knitting and are associated in a way that their structure pores are not aligned;

wherein said hernia implant is made of at least one material which is at least partly absorbable in vivo and where, by way of in vivo degradation of said absorbable material, pore sizes of openings in said hernia implant increase; and wherein said hernia implant has a bursting pressure of 100 to 300 KPa.

27. Method according to claim 26, wherein the textile fabric structures in the form of knitwear are produced by knitting.

28. Method according to claim 26, wherein the textile fabric structures are simultaneously joined together while each of said textile fabric structures are formed.

29. Method for treating wall defects in a body cavity comprising the step of implanting in a patient in need thereof the hernia implant according to claim 1.

30. Method according to claim 29, wherein the hernia implant is used to treat abdominal wall defects.

* * * * *